United States Patent [19]
Kuhnell et al.

[11] Patent Number: 5,790,246
[45] Date of Patent: Aug. 4, 1998

[54] APPARATUS AND NETWORK FOR DETERMINING A PARAMETER OF A PARTICLE IN A FLUID EMPLOYING DETECTOR AND PROCESSOR

[75] Inventors: Bruce Thomas Kuhnell, Glen Iris; Jacek Stanislaw Stecki, North Balywn; Zbigniew Przelozny, Noble Park; Xi Huang, Ormond; Christopher Eugene Doran, Vermont South, all of Australia

[73] Assignee: Montores Pty. Ltd., Sydney, Australia

[21] Appl. No.: 634,207

[22] Filed: Apr. 18, 1996

[51] Int. Cl.⁶ .......................... G01N 33/28; G01N 21/00; G01T 1/167
[52] U.S. Cl. .......................... 356/72; 356/70; 250/301; 324/204
[58] Field of Search .................. 356/70, 72, 440–442; 250/301; 324/204

[56] References Cited

U.S. PATENT DOCUMENTS

| | | | |
|---|---|---|---|
| 4,219,805 | 8/1980 | Magee et al. | 340/631 |
| 4,651,091 | 3/1987 | Chambers et al. | 324/204 |
| 5,159,642 | 10/1992 | Kosaka | 382/6 |
| 5,315,243 | 5/1994 | Kempster et al. | 324/204 |
| 5,428,441 | 6/1995 | Ogino et al. | 356/73 |
| 5,540,089 | 7/1996 | Fitch | 356/70 |
| 5,594,544 | 1/1997 | Horiuchi et al. | 356/73 |
| 5,614,830 | 3/1997 | Dickert et al. | 356/70 |

FOREIGN PATENT DOCUMENTS

| | | |
|---|---|---|
| 0 134 976 A2 | 7/1984 | European Pat. Off. |
| 0 539 022 A2 | 9/1992 | European Pat. Off. |
| 44 37 758 A 1 | 4/1995 | Germany |
| 2 101 330 | 5/1982 | United Kingdom |
| WO 91/09308 | 6/1991 | WIPO |
| WO 93/19376 | 9/1993 | WIPO |
| WO 94/14049 | 6/1994 | WIPO |

*Primary Examiner*—Frank G. Font
*Assistant Examiner*—Jason D. Vierra-Eisenberg
*Attorney, Agent, or Firm*—Fish & Richardson P.C.

[57] ABSTRACT

An apparatus and method for determining a parameter of a particle in a fluid is disclosed and, in particular, an apparatus and method for determining contamination or machine wear by the measurement of contamination or wear particles in a fluid used in the machine is disclosed. In a first embodiment, a measurement cell is provided with a fluid flow path. A first hall probe is arranged adjacent to the flow path for detecting dia-magnetic, para-magnetic, ferro-magnetic particles and a second optical sensor formed of a light emitting diode and phototransistor are provided for optically detecting the particles. A correlation between the hall probes and the optical detector enables an indication of the particles to be obtained so that a parameter of those particles can be determined to provide an indication of contamination or machine wear. In a second embodiment, a measurement cell having a fluid chamber is provided and two pulsed light sources are arranged in the cell for transmitting light through the fluid to a charged couple device so that a first image can be produced by light transmitted through the fluid and therefore past the particles and a second pulsed light source is provided for reflection of particles so that a second image of reflected light can be produced. A comparison of the first and second images enables the metal particles to be determined so that parameters of those particles can be measured to provide an indication of contamination or machine wear.

11 Claims, 9 Drawing Sheets

APPARATUS AND NETWORK FOR DETERMINING A PARAMETER OF A PARTICLE IN A FLUID EMPLOYING DETECTOR AND PROCESSOR

FIELD OF THE INVENTION

This invention relates to an apparatus and method for determining a parameter of a particle in a fluid and, in one example, to determining contamination and machine wear particles and, in particular, to the measurement of wear particles in a fluid used in a machine or process. The fluid may be a lubricant, such as oil to lubricate the machine, a hydraulic fluid used in a hydraulic system, a coolant, such as a cutting fluid used to assist machining processes or a process fluid such as slurry in a mineral extraction process etc.

BACKGROUND OF THE INVENTION AND PRIOR ART

Determination of ware of the machine is important in order to provide an indication of the correct operation, condition and/or residual life of the machine or process.

A consideration of contamination and wear particles has an advantage over other monitoring methods such as vibration, noise, temperature performance, and human senses etc that an early indication of likely process faults or machine failure can be determined. The present invention is concerned with this type of monitoring.

Conventional techniques for measurement of fluid borne particles usually comprise the transmission of light through the fluid containing the particles and detection of that light. The particles in the fluid cause interruption to the light transmitted through the fluid and changes in the light detected by the detector proves a distribution of particle size.

One problem associated with conventional particle counter techniques is that it is not possible to identify particular types of particles and therefore light transmitted through the fluid may be interrupted by particles which are in fact wear particles produced in operation of the machine or other contaminants such as dust or the like which may be present in the fluid without the ability to discriminate between the different types.

SUMMARY OF THE INVENTION

The object of the present invention is to overcome or reduce this problem.

The present invention may be said to reside in an apparatus for determining a parameter of a particle in a fluid, including:

detector means for detecting a certain type of particle in the fluid and for providing information relating to the parameter of particles in the fluid; and processing means for determining the parameter of the certain type of particle in the fluid.

In the preferred embodiment of the invention, the apparatus is for determining contamination or machine wear and the fluid comprises a machine or process fluid. The determined parameter of the certain type of particle in the machine or process fluid provides an indication of contamination or machine wear.

Thus, the invention enables certain types of particles to be identified which, for example, may be most relevant to indications of machine wear and enables the parameters of those particles to be determined so that an indication of machine wear can be provided.

In one embodiment of the invention the detector means comprises a magnetic sensor for detecting dia-magnetic, para-magnetic or ferro-magnetic particles and an optical sensor for providing an output indicative of the parameter of the dia-magnetic, para-magnetic or ferro-magnetic particles.

In another embodiment the detector means comprises a sensor for producing a first image of particles in the fluid produced by light transmitted through the fluid and a second image of a certain type of particle in the fluid produced by reflected light from the certain type of particles, the first image providing information from which a parameter of the certain type of particle shown in the second image can be determined to provide the indication of contamination or machine wear. Thus, from the first image, the particle sizes, shapes and areas as well as darkness can be abstracted. The second image of these same particles provide the brightness of these particles. Therefore, particles can be classified based on their different optical absorption and reflection coefficients.

The present invention may also be said to reside in a method of determining a parameter of a particle in a fluid including the steps of:

detecting a certain type of particle in the fluid to identify the certain type of particle and detecting the particles in the fluid to provide information relating to a parameter of the particles so that the parameter of the certain type of particles can be determined.

Once again, in the preferred embodiment of the invention, the method relates to determining contamination or machine wear and the fluid is a machine or process fluid. Once again, the determination of the parameter of the certain type of particle provides an indication of contamination or machine wear.

The present invention may also be said to reside in a measurement cell for use in an apparatus for determining a parameter of a particle, including:

(i) a chamber for receiving a fluid which contains particles, including a certain type of particle;

(ii) first detector means for detecting the certain type of particle in the fluid and for producing a first output indicative of the presence of the certain type of particle; and (iii) second detector means for detecting the particles in the fluid and for producing a second output indicative of the parameter of the particles in the fluid, so that the first and second outputs can be correlated to identify the certain types of particles detected by the second detector means, and processed to determine the parameter of the certain type of particle.

The present invention may also be said to reside in a measurement cell for use in an apparatus for determining a parameter of a particle, including:

(i) a chamber for receiving fluid which includes particles;

(ii) first means for providing electromagnetic radiation and transmitting the electromagnetic radiation through the fluid from one side of the chamber to the other side of the chamber;

(iii) second means for providing electro magnetic radiation for reflection off the particles; and (iv) sensor means for producing a first image from the transmitted electro magnetic radiation and a second image from the reflected electro magnetic radiation, so that the first and second images can be compared to identify particles common to both images and for determining a parameter of the particles common to both images.

The present invention may also be said to reside in an apparatus for determining a parameter of a particle, including:

a measurement cell having;
(i) a chamber for receiving a fluid which contains particles, including a certain type of particle;
(ii) first detector means for detecting the certain type of particle in the fluid and for producing a first output indicative of the presence of the certain type of particle; and
(iii) second detector means for detecting particles in the fluid and for producing a second output indicative of the parameter of the particles in the fluid;

correlation means for correlating the first and second outputs to identify the certain types of particles detected by the second detector means; and processing means for determining the parameter of the certain type of particle.

The present invention therefore enables particular types of particles to be identified such as metallic particles in view of the correlation between the first and second detectors. The particle particles detected by the first detector may be those of particular interest in determining contamination or machine wear, and thus those particles can be identified amongst all the particles detected by the second detector means so that the parameter of those particles can be considered to provide an indication of contamination or machine wear.

Preferably the chamber comprises a flow channel through the cell so that the cell can be located in line in a fluid path for measurement of machine wear. On-line measurement or off-line measurement can also take place.

Preferable the first detector comprises a magnetic means for producing a magnetic field to magnetise dia-magnetic, para-magnetic or ferro-magnetic particles and at least one magnetic flux detector for detecting the magnetised particles.

Preferably the magnetic flux detector comprises at least one Hall effect device.

Preferably the second detector means comprises an optical detector formed of a light source and a phototransistor for detecting light transmitted from the light source through the fluid to the phototransistor.

Preferably the correlating means and the processing means comprises a processor such as a personal computer.

The invention may also be said to reside in a method for determining a parameter or a particle, including the steps of:

detecting with a first detector a certain type of particle in a fluid used in a machine or process, which contains particles including the certain type of particle, and producing an output indicative of the certain type of wear particle detected by the first detector;

detecting particles in the fluid with a second detector to provide a second output which enables the parameter of the particles to be determined;

correlating the first and second output so that the certain type of particle detected in the second detection step can be identified; and determining the parameter of the certain type of particle.

The present invention may also be said to reside in an apparatus for determining a parameter of a particle, including:

a measurement cell having:
(i) a chamber for receiving fluid which includes particles;
(ii) first means for providing electromagnetic radiation and transmitting the electromagnetic radiation through the fluid from one side of the chamber to the other side of the chamber;
(iii) second means for providing electro magnetic radiation for reflection off the particles;
(iv) sensor means for producing a first image from the transmitted electro magnetic radiation and a second image from the reflected electro magnetic radiation; and processing means for comparing the first and second images to identify wear particles common to both images and for determining a parameter of the particles common to both images.

The use of the reflected radiation and the image produced from that radiation enables certain types of particles to be identified, for example, particles which readily reflect light. Thus, whilst any particle in the fluid will effectively cast a shadow to the transmitted radiation and therefore appear in the first image, the second image can be used to identify particles which, for example, are most relevant to contamination or machine wear so that parameters of the particles can be determined to provide an indication of machine wear.

Preferably the chamber comprises a flow channel through the cell so that the cell can be located in line in a fluid path for measurement of contamination or machine wear.

Once again the measurement may be made on line or off line.

Preferably the fluid is substantially stationary in the chamber when the images are formed.

Preferably a pump is provided for circulating fluid through the cell, the pump being switched off to stop the fluid in the channel when the images are formed.

Preferably the sensor comprises a charge coupled device.

Preferably the first means comprises a pulsed light source and optical lenses for producing a collimated beam of the light for the transmission through the channel and an optical magnification system to the sensor.

Preferably the second means comprises a pulsed light source on the same side of the channel as the sensor for producing light which is reflected off the wear particles to the sensor.

Preferably the processor comprises a personal computer.

The present invention may also be said to reside in a method for determining a parameter of a particle comprising the steps of:

forming a first image of particles in a fluid by transmitting light through the fluid;

forming a second image of a certain type of particle in the fluid by reflecting light off the certain type of particles in the fluid; and comparing the first and second images to identify the certain type of particles in the first image to enable a parameter of the certain types of particles to be determined from the first image.

Once again, the method and apparatus referred to above are for determining machine wear and the fluid is a fluid used in the machine, the certain type of particle is a wear particle produced during operation of the machine and the parameter of the certain type of particle enables an indication of machine wear to be determined.

BRIEF DESCRIPTION OF THE DRAWINGS

A preferred embodiment of the invention will be described, by way of example, with reference to the accompanying drawings in which.

DESCRIPTION OF THE PREFERRED EMBODIMENTS

Figure 1:
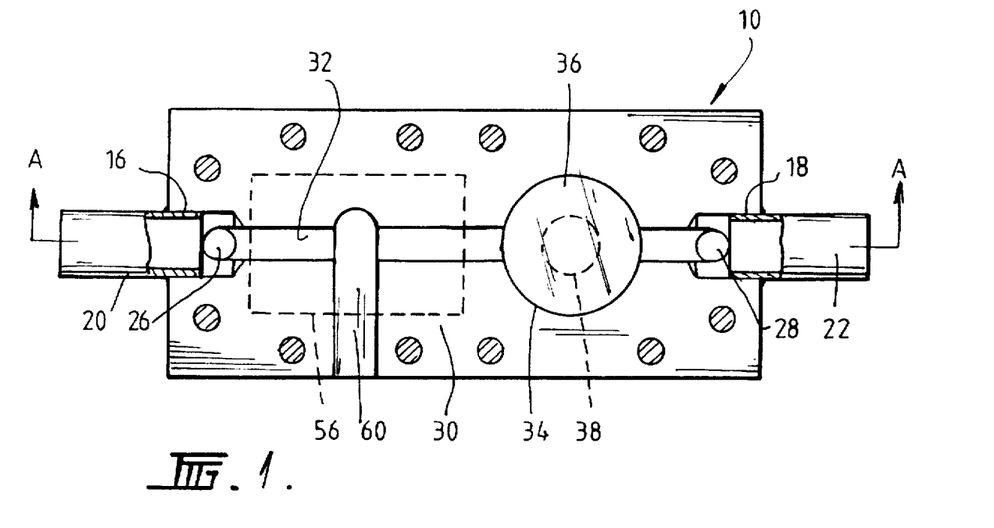
FIG. 1 is a cross sectional view of a measurement cell used in one embodiment of the invention.
Figure 2:
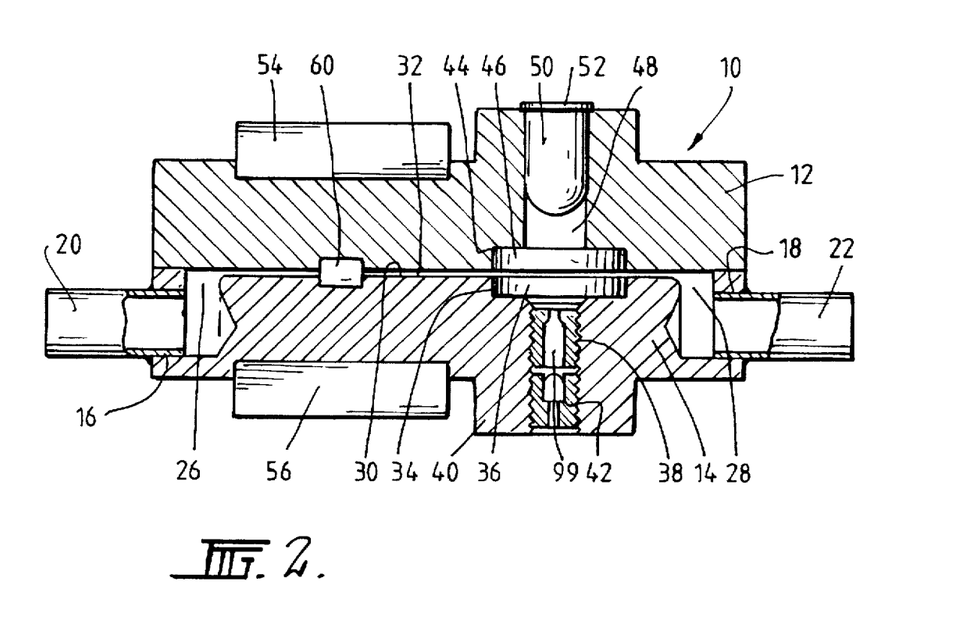
FIG. 2 is a cross sectional view along the line A—A of FIG. 1.

With reference to FIGS. 1 and 2 a measurement cell 10 used in the preferred embodiment is shown. The measurement cell 10 is formed in two halves 12 and 14 which are coupled together to form the cell 10. The cell half 14 has an inlet bore 16 and an outlet bore 18. An inlet tube 20 is welded in the inlet bore 16 and an outlet tube 22 is welded in the outlet bore 18. The inlet tube 20 and outlet tube 22 are intended to be coupled in a fluid supply line such as an oil line used in a machine so that oil can circulate through the cell as will be described in more detail hereinafter during use of the machine for real time in line monitoring of the machine.

The cell half 14 has a bore 26 and a bore 28 which extends transverse to the bores 16 and 18 and which communicate with the inlet tube 20 and outlet tube 22 respectively. An upper surface 30 of the cell half 14 is provided with a groove 31 which interconnects the bores 26 and 28 so that when the cell halves 14 and 22 are coupled together, as shown in FIG. 2, a channel 32 is provided through the cell 10 so that fluid can flow from the inlet tube 20 through the bore 26, through the channel 32, through the bore 28 and out through the outlet tube 22. The channel 32 typically has a dimension of 1.0 mm in depth as shown in FIG. 2 and 5 mm in width as shown in FIG. 1.

The surface 30 of the cell half 14 is provided with a recess 34 in which an optical glass disc 36 is bonded. A bore 38 extends from the disc 36 through the cell half 14 to a transistor mount 40 located on the cell half 14 for mounting a phototransistor 42.

A recess 44 is also provided in the cell half 12 opposite the recess 34 and a disc 36 is located in the recess 44. A bore 48 extends from the disc 46 through the cell half 12 to a light emitting diode 50 mounted to the cell half 12 by a LED mount 52.

A pair of permanent magnets 54 and 56 are located in the cell halves 12 and 14 and a Hall effect device such as a Hall probe 60 is arranged in registry with the channel 32 of the measurement cell 10. As will be explained in more detail hereinafter, a pair of Hall probes 60 may be provided on each side of the cell 10 so that the Hall probe 60 are transverse to the light emitting diode 50 and phototransistor 42.

Figure 3:
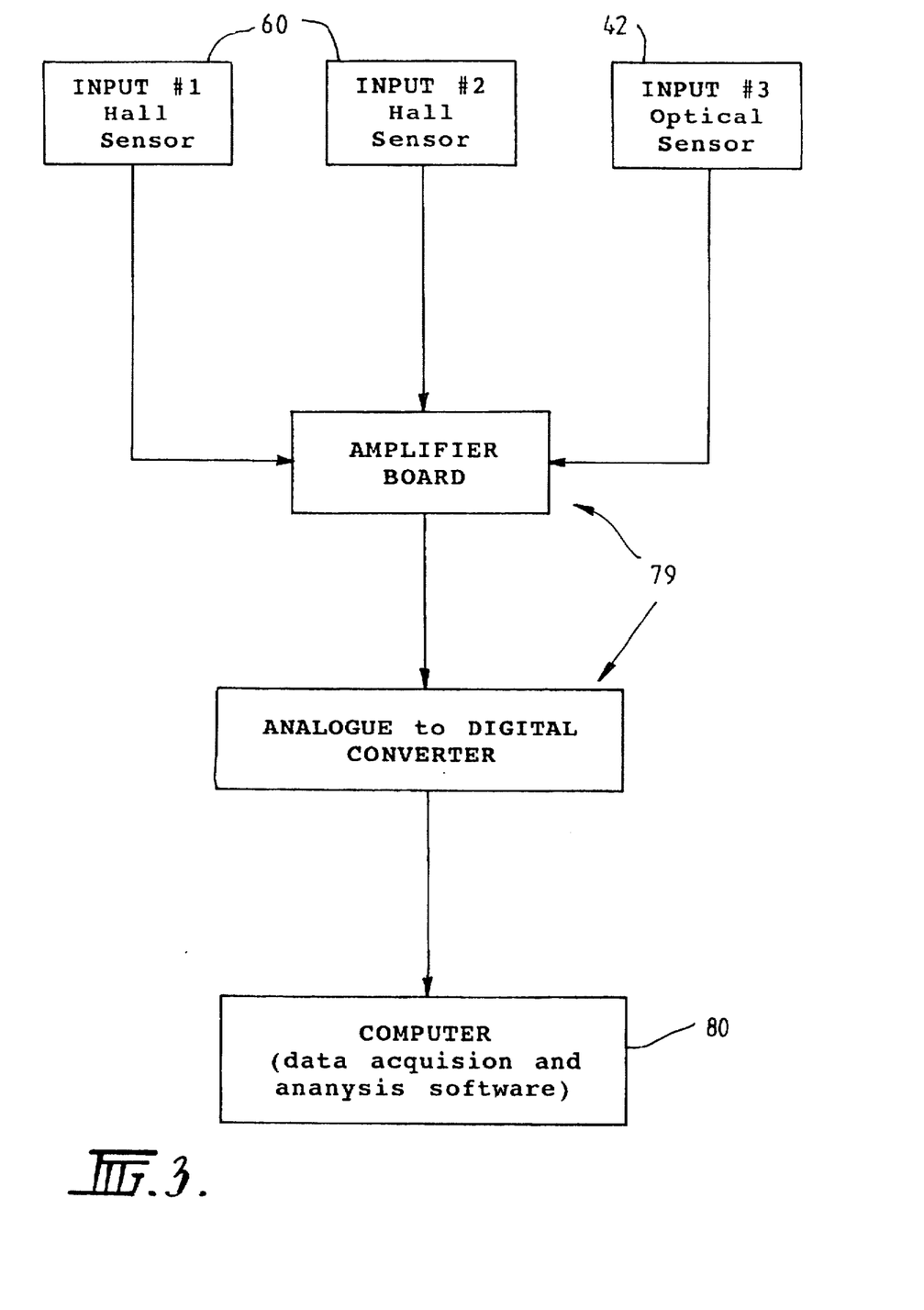
FIG. 3 is a schematic block diagram of a processing system used in the embodiment of FIG. 1.

As shown in FIG. 3 the Hall probe or probes 60 are coupled to a processor such as a suitable portable computer 80. The phototransistor 42 is also coupled to the processor 80. Outputs from the Hall probe 60 and phototransistor 42 may be amplified and conditioned for application to the processor 80 by amplifying and conditioning circuitry 79 including an analogue to digital converter.

Power to the Hall probe 60, phototransistor 42 and to the light emitting diode 50 is provided by a power supply (not shown).

A pump (not shown) may be provided for location in a fluid line into which the cell 10 is to be inserted for ensuring that fluid from a machine flows through the channel 32. Fluid, such as lubricating oil from a machine therefore is able to flow through the channel 32 past the Hall probe 60 and also past the optical glass discs 36 and 46. Particles in the fluid will include ferro magnetic particles as well as other contaminants including dust and the like. The ferro magnetic particles will be magnetised by the permanent magnets 54 as the particles flow through the channel 32 and the Hall probe 60 will detect the magnetic flux of the magnetised particles and produce an output. The particles will continue to flow through the channel 32 and between the discs 46 and 36. The light emitting diode(s) 50 can be activated to transmit light through the bore 48, disc 44, the channel 32, disc 36 into bore 38 for detection by the photo transistor 42. A collimator 99 is arranged in the light path between the light emitting diode 50 and the phototransistor 42 for collimating the light emitted by the light emitting diode 50 and for providing depth of a field which extends substantially across the entire depth of the channel 32. The collimator aperture is typically 300 microns. The particles flowing in the channel 32 and between the discs 36 and 46 will therefore interrupt the light emitted from the light emitting diode 50 to the phototransistor 42 so that a change of light intensity will be detected by the phototransistor 42 when a particle interrupts the beam of light. Thus, magnetised particles detected by the Hall probe 60 will arrive at the optical detector formed by the light emitting diode 50 and phototransistor 42 after a certain time period. The output produced by the Hall probe 60 can effectively be used to trigger the optical detector so that the magnetised particles are detected by the optical detector and measured to provide an indication of machine wear. Thus, a sizing of the magnetic particles is based on the cross correlation between the magnetic detector formed by the permanent magnets 54 and 56 and the Hall device 60 and the optical sensor formed by the light emitting diode 50 and photo transistor 42.

The change in output of the phototransistor is proportional to the particle size. In principle, the output is scaled as follows:

$$V_c = V_{dc}(1-(A_p/A_d))F$$

where, $V_{dc}$—dc output from phototransistor (with no oil in channel)

F—opacity factor for oil (0 to 1)

$A_p$—particle cross section $A_d$—detection area.

The output voltage from the Hall probe 60 increases linearly with magnetic field until saturation at a typical level of 400 gauss. If magnetic particles are present in the fluid they are magnetised in the static magnet field and a change in magnetic flux is detected by the Hall probe 60 as the particles pass.

The time cross correlation between the magnetic sensor formed by the magnets 54 and 56 and the Hall probe 60 and the optical sensor formed by the light emitting diode 50 and photo transistor 42 is described by the following formula:

$$\rho(\tau) = R_{xy}(\tau)/\sqrt{R_{xx}(o) \times R_{yy}(o)}$$

where,

τ is the time delay,

ρ(τ) is the normalised correlation at time delay τ, $R_{AB}(\tau)$ is the correlation between signal A and signal B at time delay τ, x is the signal from the Hall Probe, y is the signal from the phototransistor.

As noted above the output of the photo transistor 42 is proportional to the size of the particle detected. The optical sensor used in the preferred embodiment of the invention is preferably calibrated in the following manner. The size of the detected particle is proportional to the AC component of signal $V_o$. To obtain a calibration line, a number of discs of aperture 500, 200 and 100 microns have been used. A correction is made for the shadow enlargement due to the divergence of the LED light source.

In operation the average value $V_c$ is used to determine the opacity of the oil F. As the oil condition or type is changed, this factor is adjusted automatically to ensure the correct particle cross section, $A_p$ is registered. Since the output of the phototransistor $V_o$ is also temperature dependent, to correlate a change of DC rading with change in opacity, it is preferred to monitor a temperature close to the phototransistor. This enables changes in opacity to be distinguished from changes in fluid temperature.

Figure 4:
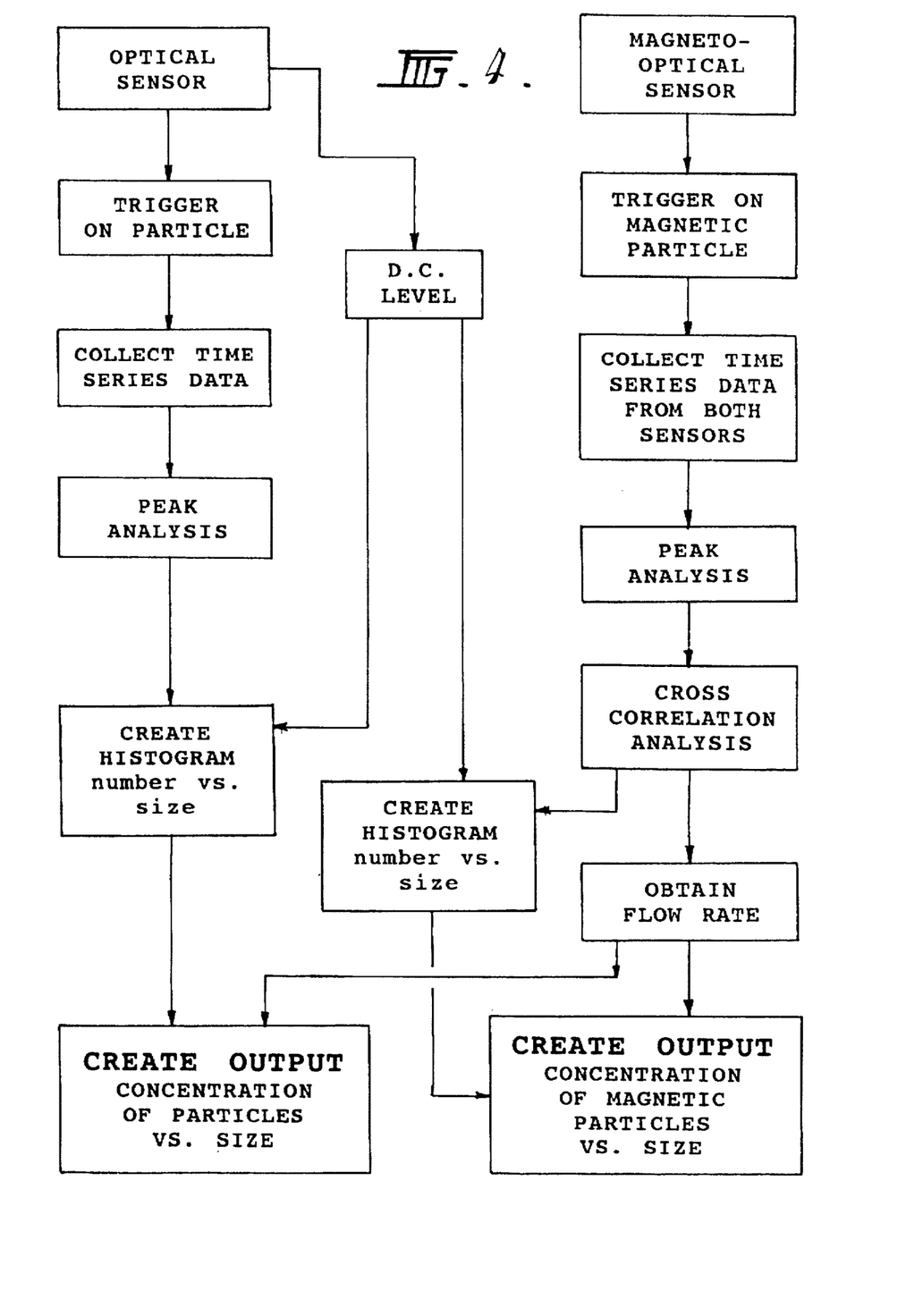
FIG. 4 is a flow chart setting forth analysis used in the embodiment of FIG. 1.

FIG. 4 shows a flow chart of the analysis sequence used in the preferred embodiment of the invention for both the magnetic and optical sensor, and the optical sensor alone.

Figure 5:
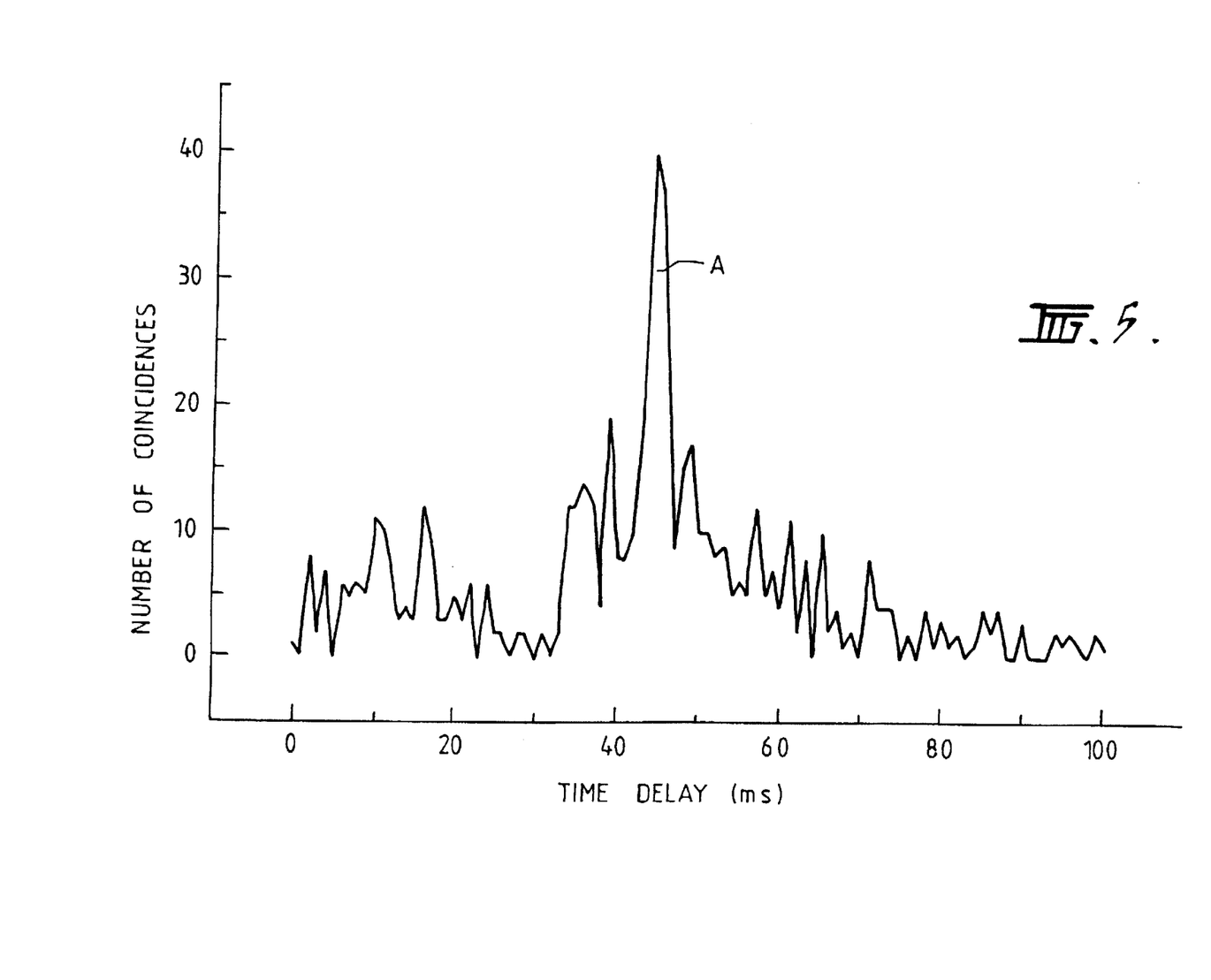
FIG. 5 is a graph showing cross correlation exemplifying particles detected by the apparatus of the embodiment of FIG. 1.

FIG. 5 shows the cross correlation between the magnetic and optical sensor referred to above in which the presence of magnetic particles is shown at the peak labelled (A) in FIG. 5. The smaller peaks in FIG. 5 are due to detection of other particles which randomly arrive at the optical detector between detection of a particle by the Hall probe 60 and the optical detector.

Figure 6:
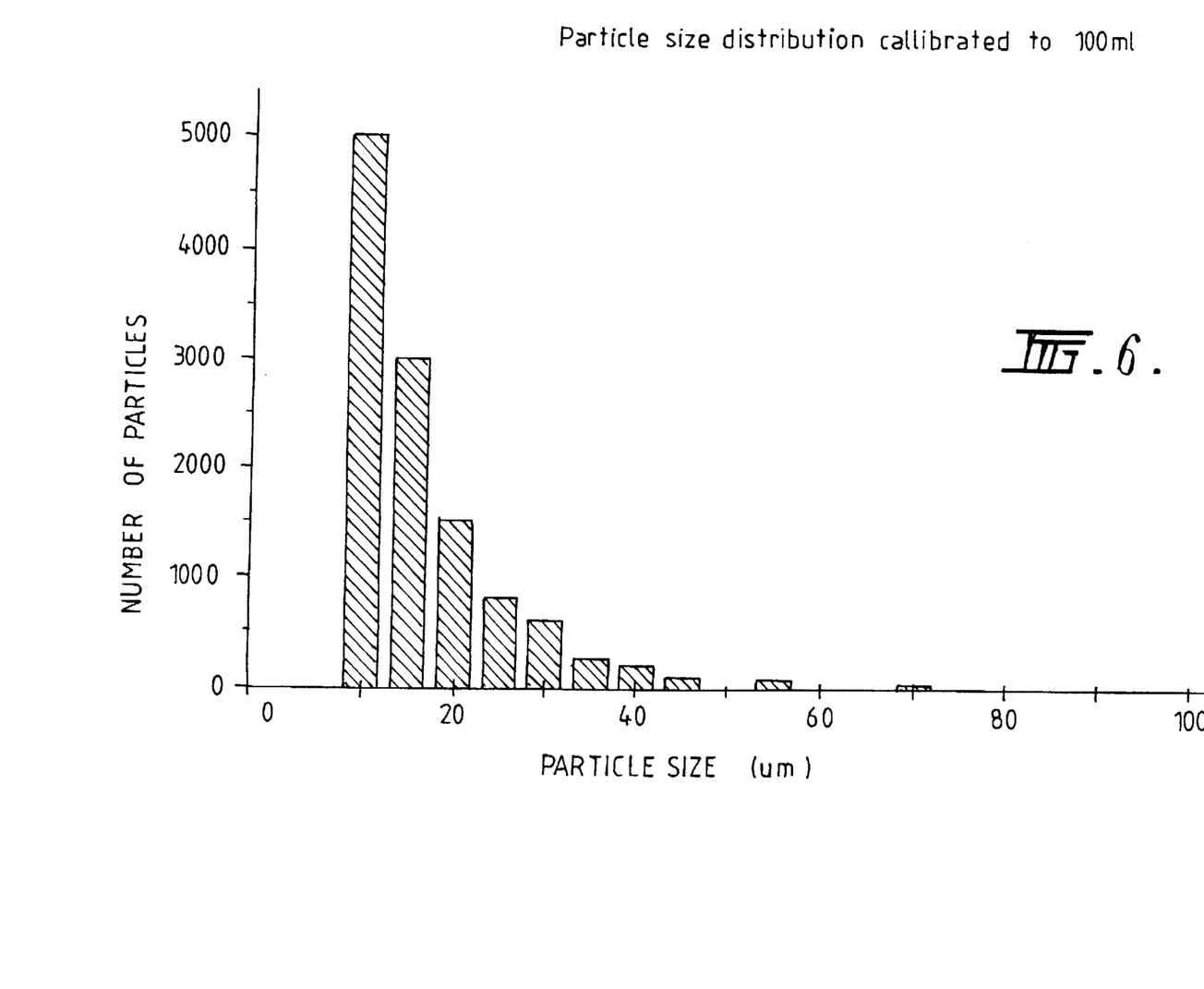
FIG. 6 is a graph showing the total number of particles detected.
Figure 7:
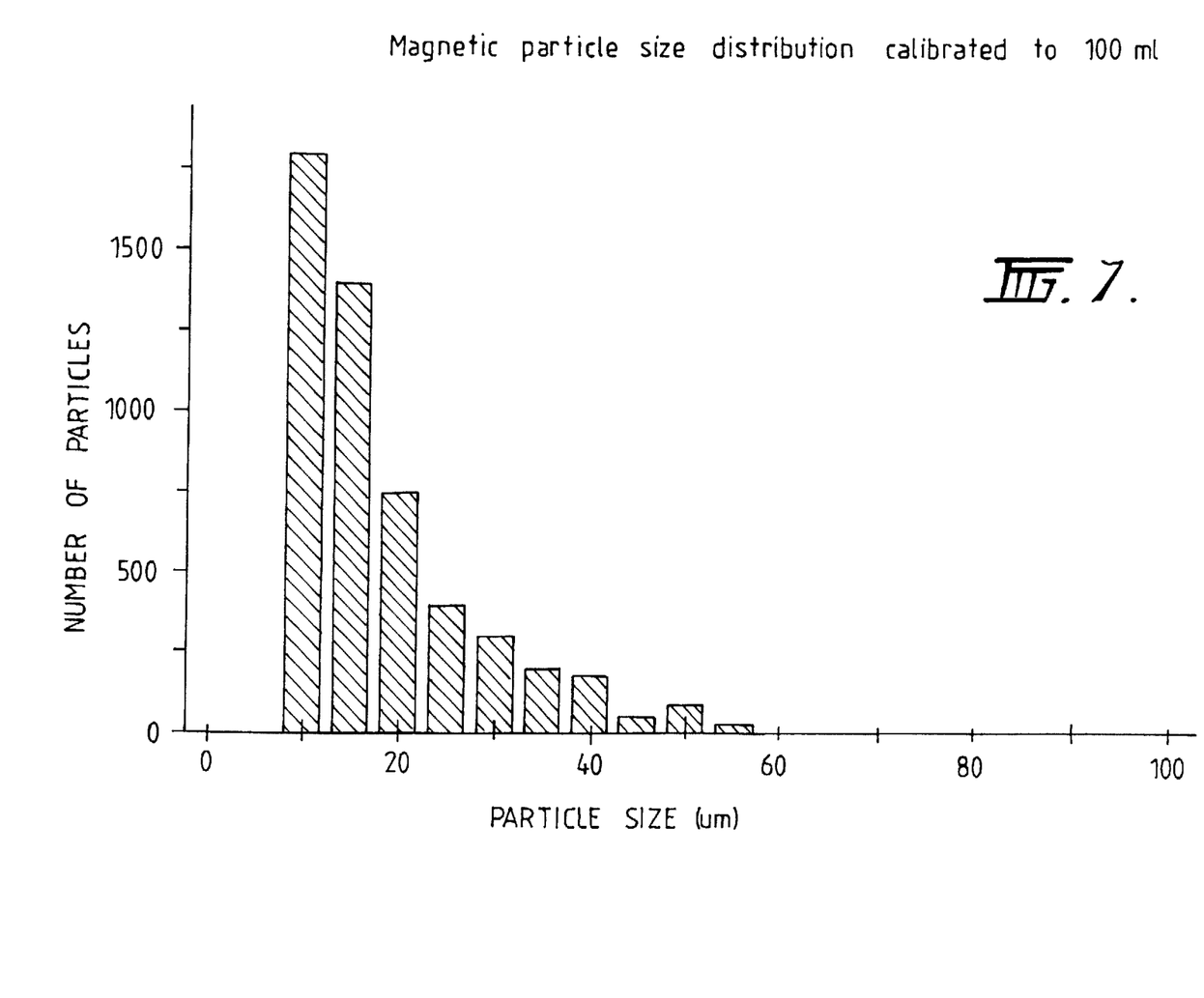
FIG. 7 is a graph showing the total number of a certain type of particle detected.

FIG. 6 shows the total number of particles in 100 ml of fluid as detected by the optical detector and FIG. 7 shows the number of magnetic particles in 100 ml of fluid. Thus, a histogram of the particles of interest in this system can be built up and in particular a histogram of ferro magnetic particles can be built up which gives an indication of the number of particles and also size of the particles. The size of the particles, and the number of particles are determined in the processor 80 in the manner described above, and the diagnosis of machine wear can be made based on the wear particles which are detected by the apparatus of the preferred embodiment.

In this embodiment ferro-magnetic metallic particles are considered to provide an indication of machine wear. In other embodiments other particles such as contaminants in the fluid or particles in a process fluid could be determined to provide an indication of contamination in the fluid or process operation.

Another embodiment of the invention can provide an advanced performance system in which the size aspect ratio of the magnetic particles detected by the measurement cell can be determined. This requires the use of two Hall probes as mentioned above and the optical sensor must be triggered on both Hall probes for a statistical distribution of volume to area ratio of the ferro-magnetic particles.

Figures 8, 9:
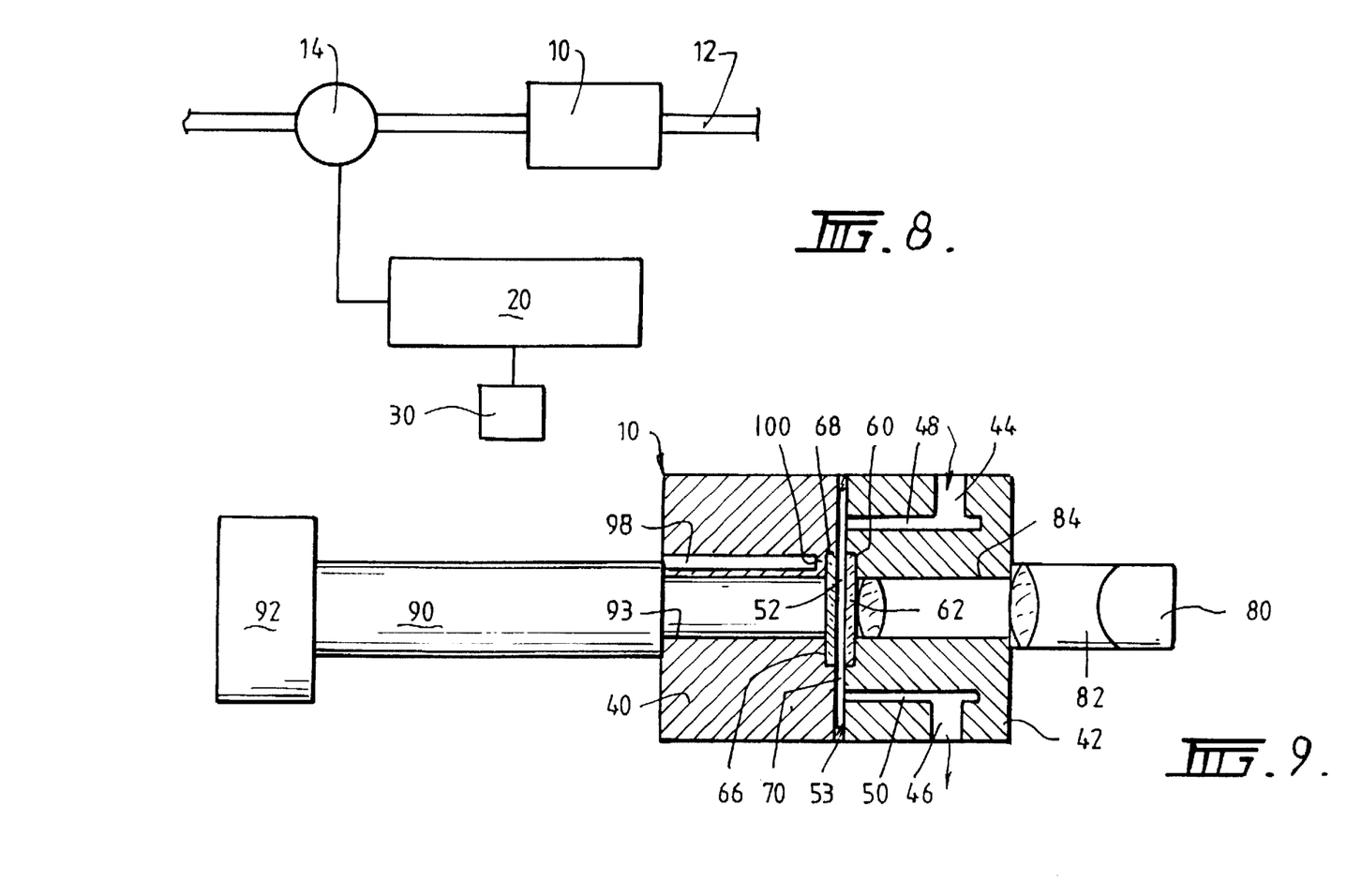
FIG. 8 is a schematic diagram of a second embodiment of the invention.
FIG. 9 is a cross-sectional view through a measurement cell used in the embodiment of FIG. 8.

Another embodiment of the invention is shown in FIGS. 8 and 9. This embodiment includes a measurement cell 10 for location in a fluid line 12 of a machine (not shown). A pump 14 is provided for ensuring flow of fluid through the line 12 and the cell 10. A processor 20 is provide for receiving outputs from the cell 10 (as described in more detail hereinafter) and for enabling images to be produced for display on a monitor 30. A hard copy of the images produced by the processor 20 can be produced by a printer (not shown). The pump 14 may also be controlled by the processor 20.

The measurement cell 10 is best shown in FIG. 9 and comprises a pair of cell halves 40 and 42. The cell half 42 has an inlet tube 44 and outlet tube 46 for connection to the fluid line 12 in FIG. 1. Transverse bores 48 and 50 extend from the tubes 44 and 46 respectively and a channel 70 is provided in the cell half 42 between the bores 48 and 50. A recess 60 is provided in the cell half 42 and a glass disc 62 is provided in the recess 60. The cell half 42 has a front portion 66 in which the cell half 40 is received. A disc 66 is retained in a recess 68 in cell half 40. The channel 70 is formed by a groove 52 which extends from bore 48 to the bore 50 or by locating a gasket 53 between cell half 40 and cell half 42 to space those components so that the channel 70 is formed between disc 68 and the disc 62 as shown in FIG. 9. The channel 70 preferably has a depth dimension as shown in FIG. 9 of about 0.8 mm and a width of about 5 mm. Thus, fluid can flow from the inlet 44 to the outlet 46 through the cell 10.

A first light source 80 is arranged in a mount 82 which is located in a transverse bore 84 in the cell half 42. Optical lenses are provided in the bore 84 for forming a collimated beam of light across the depth of the channel 70. A tube 90 is also mounted in a bore 93 in the cell half 40 and a charge couple device 92 is arranged at the end of the tube 90. The tube 90 may include lenses in the part of the tube 90 within the bore 93 for focusing light onto the charge couple device 92. The optical system comprising tube 90 and its included components and the charge coupled device 92 is preferably optimised so the depth of field allows particles to remain substantially in focus across channel 70.

A second light source 98 is provided in the cell half 40 on the same side of the channel 70 to the light source 80.

The light sources 80 and 98 are controlled under the influence of the processor 20 shown in FIG. 8. The pump 14 is stopped so that the flow of fluid through the cell 10 is also effectively stopped. Thus, the flow is made stationery in order for measurements to be made.

The light sources 80 and associated lenses produce a collimated beam of light which passes through the channel 70 from one side of channel 70 to the other and then to the charge couple device 92 so that any particles including wear particles in the fluid in the channel 70 are imaged in the form of a shadow on the charge couple device 92. Thus, a first image formed by transmitted light through the channel 70 is formed on the charge couple device 92 and the output of the charge couple device 92 is provided to processor 20 so that the image can be displayed on the monitor 30 and a hard copy of the image can be provided if desired.

A second image is formed by reflected light from the light source 98 under the control of the processor 20. Light from the light source 98 is transmitted over space 100 through disc 68 into the channel 70 and is reflected from the reflecting particles such as metallic particles in the fluid through the tube 90 to the charge coupled device 92.

Thus, the first image formed by transmitted light will show any particle in the fluid including metallic wear particles of particular interest along with other contaminants such as dust and the like. The first image provides information from which the size of the particles can be determined in view of the shadow outline of the particles and thus, the process 20 can provide information concerning the size of the particles sot hat tan indication of machine wear can be obtained.

Figure 10:
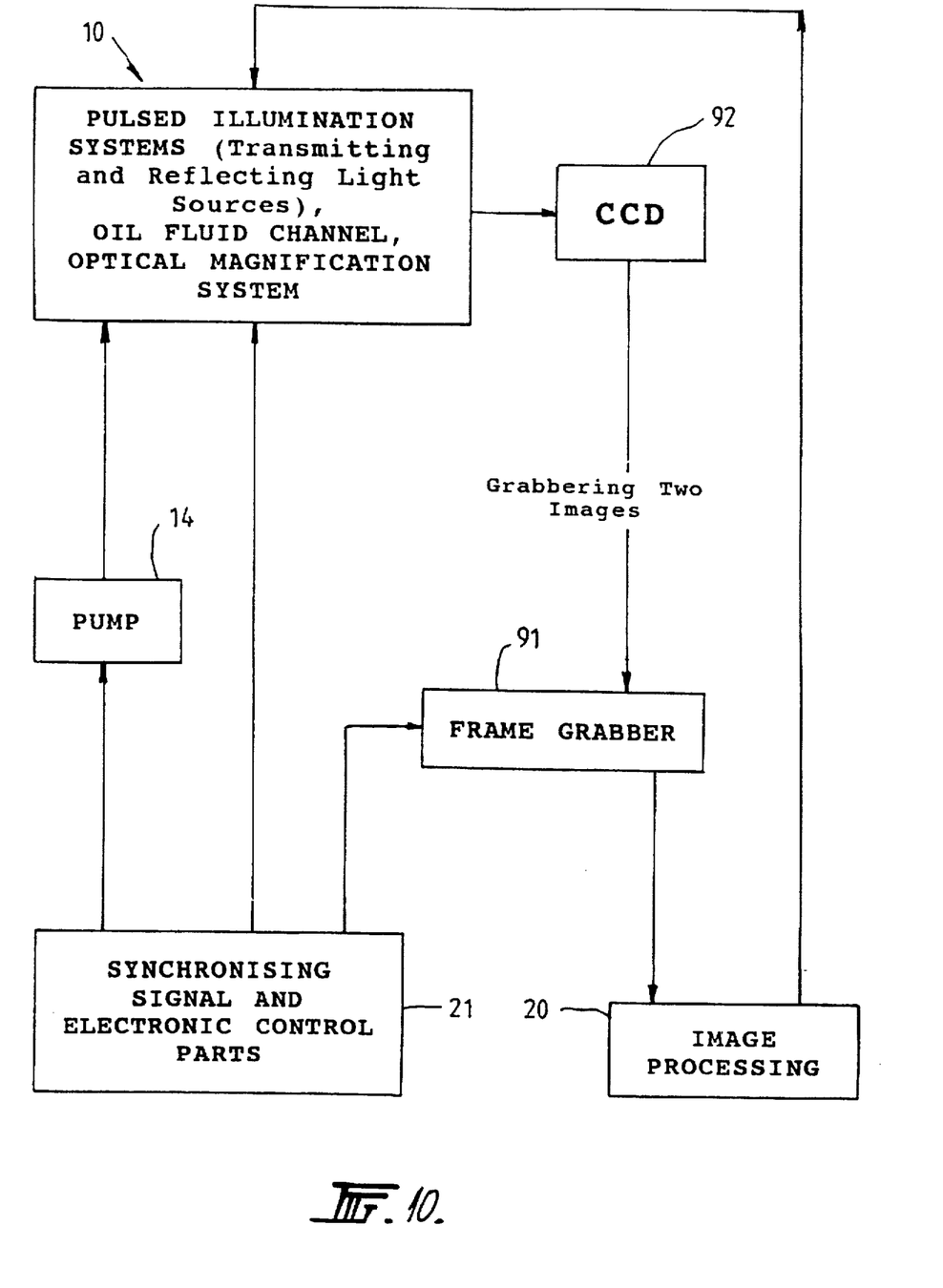
FIG. 10 is a view showing the synchronising of the apparatus according to the embodiment of FIG. 9.

FIG. 10 shows the synchronisation and timing according to the embodiment of FIGS. 8 and 9. Electronic control part 21 synchronises the pump, and light sources 80 and 98 in the cell 10 together with a frame grabber 91 which grabs single frames from the CCD 92 to form images of the particles for both transmitted and reflected light sources 80 and 98. The frame grabber 91 supplies data to the image processing computer 20 for processing the image as described above.

Figure 11:
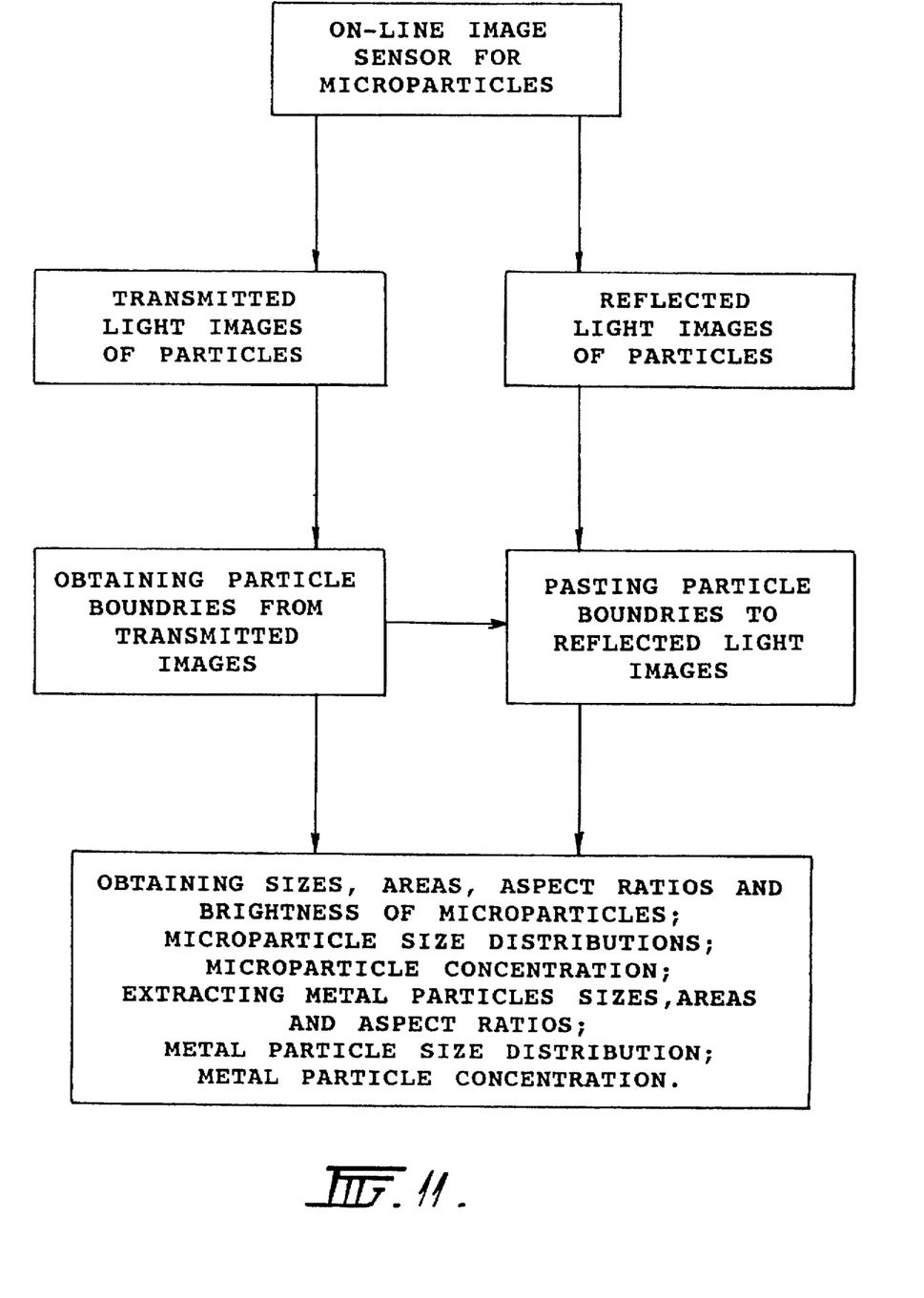
FIG. 11 is a flow diagram showing the analysis and determination of a particle parameter.

As shown in FIG. 11, the general analysis is shown in which transmitted and reflected light images of particles are considered and particle boundaries are obtained from the transmitted light image which are then pasted onto the particle boundaries in the reflected light image so that from the particle boundaries from the transmitted light image and the pasted particle boundaries a parameter, and in particular, a set of parameters for the particle can be obtained which includes obtaining sizes, areas, aspect ratios and brightness of particles; particle size distributions; particle concentration; opaque particle sizes, areas and aspect ratios; metal particle size distribution; and metal particle concentration.

In order to determine which particles are in fact metallic particles and therefore of significant interest in determining machine wear the image formed by reflected light, in which metallic particles can be seen or detected because the metallic particles will reflect a large amount of light and be readily visible and distinguishable in the image, is compared with the image formed by the transmitted light, by mapping the reflected image onto the transmitted image. This enables the metallic particles in the second image to be used to identify the corresponding particles in the first image.

Thus, by mapping the reflected image on the transmitted image, opaque particles can be identified and the size and other parameters of the opaque particles determined to provide indication of machine wear.

The processor 20 may include image processing software for determining the size of the particles from the first image after the metallic particles in the second image are correlated with and identified in the first image.

In the embodiment of FIGS. 8 to 11, instead of using data relating to the metallic particles, the metallic particles could be those ignored and the other particles such as contamination particles could be those specifically considered so the parameter of those particles is determined to provide information concerning the systems which produce the particles.

In machine wear analysis, if the machine fluid, such as oil or the like is variated or agitated, it may affect the results which are obtained or make if difficult for the sensors to sense the particles in the fluid. In such environments, a reservoir (not shown) could be provided for storing the fluid prior to analysis so that the fluid is allowed to settle before application to the measurement cells.

The manner in which the data is transmitted from the measurement cells and amplifying and conditioning circuitry to the portable computer may be by cables in a hard wire system, by telemetry, by modem or by any other suitable transmission mode.

We claim:

1. An apparatus for determining a parameter of a particle in machine fluid, including:

a magnetic detector for detecting a certain type of particle in the machine fluid and for providing a first output;

an optical detector for detecting the particles in the machine fluid, for providing information relating to the parameter of the particles in the machine fluid, and for providing a second output; and a device responsive to the first and second outputs for identifying a particle of the certain type and for determining the parameter of the identified particle in the machine fluid.

2. The apparatus of claim 1, wherein the magnetic detector comprises a Hall-effect device for detecting dia-magnetic, para-magnetic or ferro-magnetic particles and for providing the first output indicative of these particles and the optical detector comprises a photo-transistor for providing the second output indicative of the parameter of the dia-magnetic, para-magnetic or ferro-magnetic particles.

3. An apparatus for determining a parameter of a particle in machine fluid, including:

a measurement cell having:
(i) a chamber for receiving a machine fluid which contains particles, including a certain type of particle;
(ii) magnetic detector means for detecting the certain type of particle in the machine fluid and for producing a first output indicative of the presence of the certain type of particle; and
(iii) optical detector means for detecting particles in the machine fluid and for producing a second output indicative of the parameter of the particles in the machine fluid;

correlation means for correlating the first and second outputs to identify the particles of the certain type detected by the optical detector means; and processing means for determining the parameter of the particles of the certain type from the second output.

4. The apparatus of claim 3, wherein the chamber comprises a flow channel through the cell so that the cell can be located in line in a fluid path for in line measurement of contamination or machine wear.

5. The apparatus of claim 3, wherein the magnetic detector means comprises a magnetic means for producing a magnetic field to magnetise dia-magnetic, para-magnetic or ferro-magnetic particles and at least one magnetic flux detector for detecting the magnetised particles.

6. The apparatus of claim 5, wherein the magnetic flux detector comprises at least one Hall effect device.

7. The apparatus of claim 3, wherein the optical detector means comprises a light source and a phototransistor for detecting light transmitted from the light source through the fluid to the phototransistor.

8. The apparatus of claim 3, wherein the correlating means and the processing means comprise a processor.

9. A method for determining a parameter of a particle in machine fluid, including the steps of:

detecting with a magnetic detector a certain type of particle in a machine fluid used in a machine or process, which contained particles including the certain type of particle, and producing a first output indicative of the particle of the certain type detected by the magnetic detector;

detecting particles in the machine fluid with an optical detector to provide a second output which enables the parameter of the particles to be determined;

correlating the first and second outputs so that the particle of the certain type detected in the second detection step can be identified; and determining the parameter of the particles of the certain type.

10. An apparatus for determining a parameter of a particle in machine fluid, including:

a magnetic detector for detecting a particle of a certain type in the machine fluid and for providing a first output indicative of the particle;

an optical detector responsive to the first output for detecting the particle in the machine fluid and for providing a second output indicative of the parameter of the particle; and a device responsive to the second output for determining the parameter of the particle.

11. The apparatus of claim 10, wherein the magnetic detector comprises a Hall-effect device for detecting diamagnetic, para-magnetic or ferro-magnetic particles and the optical detector comprises a photo-transistor.

* * * * *